(12) United States Patent
Jaing et al.

(10) Patent No.: US 6,466,308 B1
(45) Date of Patent: Oct. 15, 2002

(54) METHOD FOR MEASURING A THERMAL EXPANSION COEFFICIENT OF A THIN FILM BY USING PHASE SHIFTING INTERFEROMETRY

(75) Inventors: Cheng-Chung Jaing, Hsinchu (TW); Cheng-Chung Lee, Chung-Li (TW); Chuen-Lin Tien, Chung-Li (TW); Ing-Jer Ho, Hsinchu (TW)

(73) Assignee: Precision Instrument Development Center, National Science Council, Hsinchu (TW)

( * ) Notice: Subject to any disclaimer, the term of this patent is extended or adjusted under 35 U.S.C. 154(b) by 0 days.

(21) Appl. No.: 09/547,849

(22) Filed: Apr. 12, 2000

(30) Foreign Application Priority Data

Dec. 20, 1999 (TW) ........................................ 88122452 A

(51) Int. Cl.$^7$ ................................................. G01L 1/24
(52) U.S. Cl. ...................... 356/35.5; 356/496; 356/511; 356/512
(58) Field of Search ................................ 356/512, 513, 356/514, 503, 35.5, 496

(56) References Cited

U.S. PATENT DOCUMENTS 5,438,402 A  *  8/1995  Gupta .......................... 356/32
5,546,811 A  *  8/1996  Rogers et al. ................. 73/762
5,682,236 A  * 10/1997  Trolinger et al. ........... 356/28.5

* cited by examiner

Primary Examiner—Robert H. Kim
Assistant Examiner—George Wang
(74) Attorney, Agent, or Firm—Bacon & Thomas, PLLC

(57) ABSTRACT

The present invention disclose a method for measuring a thermal expansion coefficient of a thin film, in which the thin film is first deposited on two substrates having different thermal expansion coefficients under the same conditions. For each of the two deposited substrates, a relationship between the thin film stresses and the measuring temperatures is established by using a phase shifting interferometry technique, in which the stresses in the thin films are derived by comparing the deflections of the substrates prior to and after the deposition. Based on the two relationships the thermal expansion coefficient, and elastic modulus, $$\frac{E_f}{(1-v_f)},$$

can be calculated, wherein $E_f$ and $v_f$ are the Young's modulus and Poisson's ratio of the thin film, respectively.

15 Claims, 4 Drawing Sheets

(a1)

(a2)

(b1)

(b2)

(c1)

(c2)

(a1) (a2)

(b1) (b2)

(c1) (c2)

METHOD FOR MEASURING A THERMAL EXPANSION COEFFICIENT OF A THIN FILM BY USING PHASE SHIFTING INTERFEROMETRY

FIELD OF THE INVENTION

The present invention is related to a method for measuring a thermal expansion coefficient of a thin film by using phase shifting interferometry, and more particularly to a method for measuring a thermal expansion coefficient, intrinsic stress and an elastic modulus of a thin film simultaneously by using phase shifting interferometry.

BACKGROUND OF THE INVENTION

Tantalum pentoxide ($Ta_2O_5$) dielectric film has a high refractive index in the visible region with a wide transmission range extending from 300 nm to about 10 $\mu$m. $Ta_2O_5$ coatings are widely used in both optical and electronic applications. Some of these applications are as antireflection coatings, optical waveguides, metal oxide semiconductor (MOS) devices, insulator in electronic devices, and as narrow-bandpass filters. The temperature stability of optical coatings has become more and more important, especially for optical telecommunications. Narrow-bandpass filters (NBF) are the key components in the elimination of noise in fibre amplifiers and for wavelength selection in high-density wavelength-division-multiplexed systems. One of the key design parameters in the NBF is the coefficient of thermal expansion (CTE). In general, thermal effects provide important contributions to film stress. Films prepared at an elevated temperature and cooled to room temperature will be thermally strained.

For a thin film deposited on a substrate, a stress of the thin film will cause the substrate deflect downward or upward. The deflection is downward for a tensile stress and upward for a compressive stress. In either case, the thin film might detach from the substrate when the stress is too large. The stress of the thin film is composed of two components, which are intrinsic stress, $\sigma_i$, and thermal stress, $\sigma_T$, if no external stress is exerted thereon. The intrinsic stress is a result of interaction between the growth modes and the microstructure of the thin film, and the thermal stress is caused by different values of thermal expansion coefficients between the thin film and the substrate. The thermal stress can be represented by the following formula:

$$\sigma_T = (\alpha_s - \alpha_f)\frac{E_f}{(1-v_f)}(T_2 - T_1)$$

wherein $\alpha_s$ is the thermal expansion coefficient of the substrate, $\alpha_f$ and $E_f$ are the thermal expansion coefficient and Young's modulus of the thin film, respectively, $v_f$ is Poisson's ratio of the thin film, $T_1$ is a deposition temperature of the thin film. It can be understood from the above formula, the thermal stress, $\sigma_T$, at a measuring temperature, $T_2$, can be calculated if $\alpha_s$, $\alpha_f$ and $$\frac{E_f}{(1-v_f)}$$

are known. The stress of the thin film at measuring temperature, $T_2$, can also be obtained if the intrinsic stress, $\sigma_i$, is known. Briefly, the $\alpha_f$ and $$\frac{E_f}{(1-v_f)}$$

so measured will enable a person calculate, in advance, a stress of the thin film deposited on the substrate at a pre-determined temperature.

A number of techniques for measuring the thermal expansion coefficients of thin films have been developed, such as the interference fringe method, the optical levered laser technique, the bending beam technique and the capacitance cell method. In these techniques, the principle of measurement is detecting the deflections caused by the stress of the thin film at different temperatures, and calculating th hermal expansion coefficient, intrinsic stress and elastic modulus, $$\frac{E_f}{(1-v_f)},$$

by using the relationship between the stress of the thin film and the temperatures. One suitable method for measuring the deflections of the thin film deposited on a substrate is the interferometric technique [A.E. Ennos, "Stress developed in optical film coatings", Appl. Opt. Vol 5, No. 1, pp.51–61, 1966; K. Roll and H. Hoffmann, "Michelson interferometer for deformation measurements in an UHV system at elevated temperatures", Rev. Sci. Instrum., Vol 47, No. 9, pp.1183–1185, 1976.] The above interferometric technique is somewhat elaborate, and inaccurate because the difference of the number of fringe in two fringe patterns is required to be an integer.

SUMMARY OF THE INVENTION

The present invention disclose a method for measuring a thermal expansion coefficient of a thin film, in which the thin film is first deposited on two substrates having different thermal expansion coefficients under the same conditions. For each of the two deposited substrates, a relationship between the thin film stresses and the measuring temperatures is established by using a phase shifting interferometry technique, in which the stresses in the thin films are derived by comparing the deflections of the substrates prior to and after the deposition. Based the two relationships the intrinsic stress, thermal expansion coefficient, and elastic modulus, $$\frac{E_f}{(1-v_f)},$$

can be calculated. Alternatively, the stresses of the thin films deposited on two different substrates are plotted against the stress measuring temperatures, showing a linear dependence. From the slopes of the two lines in the stress versus temperature plot, the intrinsic stress, thermal expansion coefficient and elastic modulus of the thin film is determined, simultaneously. The present method is relatively simple and convenient and can be extended to varying-temperature applications without damaging the thin film.

The method for measuring a thermal expansion coefficient of a thin film deposited on a substrate by phase shifting interferometry accomplished in accordance with the present invention comprises the following steps:

a) measuring a phase function of a target surface of a first substrate at a first measuring temperature;

b) depositing a thin film on said target surface of said first substrate;

c) measuring a phase function of said thin film by using the same conditions as those in step a);

d) calculating one or more relative heights of one or more points with respect to a central point of said substrate prior to and after the deposition in step b) by using the phase functions obtained in steps a) and c), respectively, and calculating a difference of the relative heights at a same point prior to and after the deposition in step b) for each of said one or more points;

e) calculating a stress of said thin film for each of said one or more points by using said difference from step d) and calculating an average stress of said thin film therefrom;

f) obtaining another one or more average stresses of said thin film of another one or more measuring temperatures by repeating steps a), c), d) and e) except that said first measuring temperature is replaced by said another one or more temperatures, and obtaining a first set of data of said average stresses versus said measuring temperatures with respect to said first substrate;

g) measuring a phase function of a target surface of a second substrate at a second measuring temperature, wherein the second substrate has a thermal expansion coefficient different from that of said first substrate;

h) depositing a thin film on said target surface of said second substrate with the conditions same as those in step b);

i) measuring a phase function of said thin film in step h) by using the same conditions as those in step g);

j) calculating one or more relative heights of one or more points with respect to a central point of said substrate prior to and after the deposition in step h) by using the phase functions obtained in steps g) and i), respectively, and calculating a difference of the relative heights at a same point prior to and after the deposition in step h) for each of said one or more points;

k) calculating a stress of said thin film of step h) for each of said one or more points by using said difference from step j) and calculating an average stress of said thin film of step h) therefrom;

l) obtaining another one or more average stresses of said thin film of step h) of another one or more measuring temperatures by repeating steps g), i), j) and k) except that said second measuring temperature is replaced by said another one or more temperatures, and obtaining a second set of data of said average stresses versus said measuring temperatures with respect to said second substrate; and m) calculating a thermal expansion coefficient, $\alpha_f$, of said thin film by using said first set data and said second set data.

Preferably, said thermal expansion coefficient, $\alpha_f$, is calculated according to the following formula (1):

$$\sigma = \sigma_i + (\alpha_s - \alpha_f)\frac{E_f}{(1-v_f)}(T_2 - T_1) \qquad (1)$$

wherein $T_2$ is any one said measuring temperatures, $\sigma$ is said average stress of said thin film at $T_2$, $\sigma_i$ is an intrinsic stress of said thin film, $\alpha_s$ is a thermal expansion coefficient of said first substrate or said second substrate, $E_f$ is a Young's modulus of said thin film, $v_f$ is a Poisson's ratio of said thin film, $T_1$ is a temperature at which said thin film is deposited in step b) and step h).

In the method of present invention, preferably, an elastic modulus defined as follows is obtained in step m) together with said thermal expansion coefficient, $\alpha_f$:

$$\frac{E_f}{(1-v_f)}$$

wherein $E_f$ and $v_f$ are defined as above.

Preferably, said intrinsic stress, $\sigma_i$, of said thin film is obtained in step m) together with said thermal expansion coefficient, $\alpha_f$. More preferably, one of said measuring temperatures ($T_2$) is chosen to be equal to said temperature ($T_1$) at which said thin film is deposited in step b) and step h), so that said intrinsic stress, $\sigma_i$, is equal to said average stress of said thin film at $T_2$, $\sigma$, according to the formula (1).

Preferably, said measurement of phase function in step a), c), g) and i) comprises the following steps:

I) generating two reflection light beams from a reference plate and a target surface of a substrate by perpendicularly irradiating two light beams splitted from one light source on said reference plate and said target surface;

II) recombining said two reflection light beams into one single beam and directing said one single beam on a screen to form an interference pattern;

III) digitizing said interference pattern to obtain digitized light intensities thereof;

IV) moving said reference plate or said substrate to several positions in a direction parallel to said light beam irradiating thereon, and said several positions being equally spaced from an original position of said reference plate or said substrate;

V) repeating steps I) to II) to obtain digitized light intensities of interference pattern for each one of said several positions; and VI) calculating a phase function of said target surface of said substrate by using said light intensities of said interference patterns obtained from step III) and step V).

Preferably, said reference plate is moved to said several positions in step IV) by using a piezoelectric transducer (PZT) connected to a surface of said reference plate opposite to said light beam irradiating thereon, and by using a DC power supply controlled by a computer to supply a predetermined voltage to said PZT.

Preferably, said digitizing said interference pattern to obtain light intensity thereof in step III) comprises forming a image of said interference pattern by using a CCD camera and digitizing a light intensity of each pixel of said image.

Preferably, said digitized light intensities are provided to said computer, said phase functions in steps a), c), g) and i), said relative heights and said differences in steps d) and j), and said stress and said average stress in steps e) and k) are calculated by using said computer in associated with programs stored therein.

Preferably, said reference plate is moved to four positions in step IV) which are equally spaced of $\lambda/8$ from an original position of said reference plate, wherein $\lambda$ is a wavelength of said irradiating light beam on said reference plate, so that five set of light intensities of said interference patterns in steps III) and V) representing 0°, 90°, 180°, 270°, and 360° phase shifts are obtained, and said phase function is calculated by the following formula:

$$\Phi = \tan^{-1}\left[\frac{2(I_2 - I_4)}{2I_3 - I_5 - I_1}\right]$$

wherein $I_1$, $I_2$, $I_3$, $I_4$ and $I_5$ represent said digitized light intensities at a particular pixel of the five interference patterns, and $\Phi$ is a phase of said particular pixel.

Preferably, said relative heights in steps d) and j) are calculated according to the following formula:

$$\text{relative height} = \frac{0.6328}{4\pi}(\Phi_r - \Phi_c)$$

wherein $\Phi_r$ is a phase of a point on said substrate at a radius r from said central point thereof, and $\Phi_c$ is a phase of said central point of said substrate.

Preferably, said light source in step l) is a laser light or a slit light source generated by passing a light through a slit.

Preferably, the method of the present invention may further comprises repeating steps g) to m) for one or more substrates having different thermal expansion coefficients different from those of the first and second substrates, so that additional sets of data of said average stresses versus said measuring temperatures with respect to said one or more substrates are obtained, and so that said thermal expansion coefficient, $\alpha_f$, of said thin film can be calculated by using said additional sets of data together with said first set data and said second set data.

DETAILED DESCRIPTION OF THE INVENTION

An interferometer equipped with a temperature controller is used to measure a deformation of a first substrate caused by a deposition of a thin film, in which five interferograms with constant phase difference ($\pi/2$) are generated and digitized prior to and after the deposition, phase functions of the substrate prior to and after the deposition are then calculated by using the intensity of pixels of the digitized interferograms, deflections at the same points prior to and after the deposition are then calculated, and an average stress of the thin film is calculated by using the deflections. The relationship between the average stresses of the thin film and the measuring temperatures can thus be established by adjusting the temperature controller and by repeating the above procedures. When two or more than two substrates having thermal expansion coefficients different from one another are used to establish the relationship between the average stresses of the thin film and the measuring temperatures as above, the intrinsic stress, thermal expansion coefficient, and elastic modulus, $$\frac{E_f}{(1 - v_f)}.$$

Figure 1:
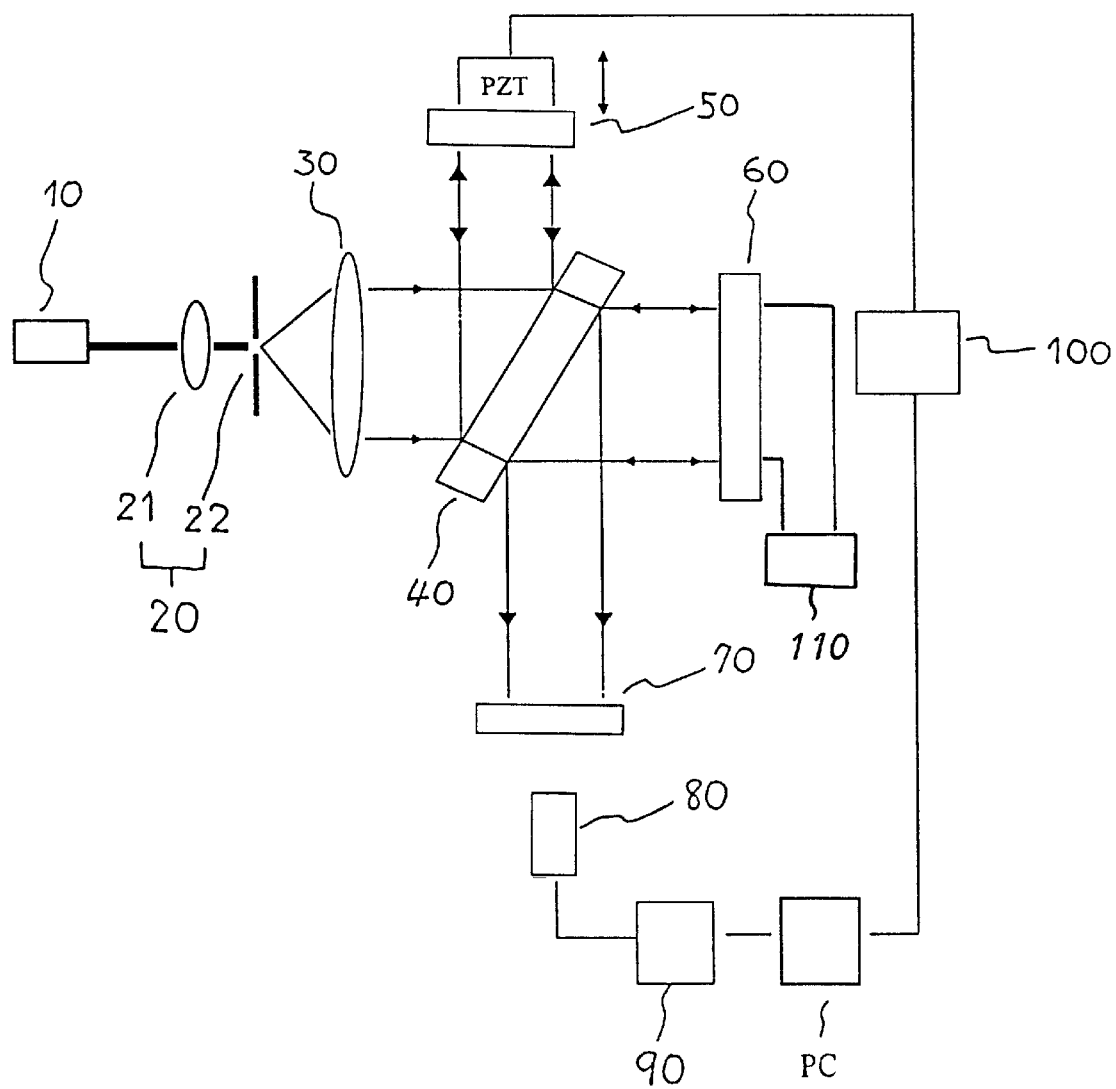
FIG. 1 is a schematic diagram showing a phase shifting Twyman-Green interferometer suitable for used in the present invention.

The optical arrangement of the phase shifting interferometry technique by using Twyman-Green interferometer is shown in FIG. 1. A He-Ne laser 10 through a micro-objective 21 and a pinhole 22 as a spatial filter 20 forms a point source and then propagate through a collimating lens 30 to form a plan wavefront. The wavefront is divided in amplitude by a beam splitter 40. The reflected and transmitted beams travel to the reference plate 50 and a test plate (the substrate) 60. After reflection from both reference plate and test plate, the beams recombine at the beam splitter 40 into a single beam and travel toward a screen 70. An interference pattern is formed on the screen 70 and can be seen on a monitor of a personal computer (PC) through a CCD camera 80 and a PC-based frame grabber 90. We use the phase-shifting Twyman-Green interferometer to measure the deflection of a deposited substrate. The principle of phase-shifting approach follows Hariharan algorithm [P. Hariharan, B. F. Oreb, and T. Eiju, "Digital phase-shifting interferometry: a simple error-compensating phase calculation algorithm", Appl. Opt., Vol 26, No. 13, pp.2504–2506, 1987] and is used to detect the phase of the fringes. We set up a PC-based system to measure the film stress. The phase shifting fringe patterns are obtained by moving the reference plate 50 to five positions equally spaced of $\lambda/8$ in a direction parallel to the beams irradiating thereon with a computer-controlled piezoelectric transducer (PZT) translation device 100 connected to the reference plate 50. A programmable power supply controlled by the PC provides the voltage to the PZT 100. At each position the interferogram is digitized. Five interferograms with constant phase difference ($\pi/2$) between the grabbed frames are used to calculate the phase map of the fringe patterns. Based on the phase-shiftin, technique a contour map of the test plate can be obtained. By using the intensities of the five fringe patterns, the phase of the fringe is calculated from the digitized intensities at each pixel in interferograms using the following equation:

$$\Phi = \tan^{-1}\left[\frac{2(I_2 - I_4)}{2I_3 - I_5 - I_1}\right]$$

wherein $\Phi$ is a phase at a point on the substrate, $I_1$ to $I_5$ represent the digitized intensities of the pixel of the same point of the five fringe patterns. The phase function so obtained represents a contour map of the substrate. Thin films deposited on a substrate will bend the substrate because of the stress. By measuring the difference of deflections between the substrate prior to and after the deposition of the thin film and assuming that the stress in isotropic, the stress in the film can be calculated using the following expression [R. W. Hoffman, in G. Haas and R. E. Thun(eds.), Physics of Thin Films, Academic Press, New York, Vol. 111, p.211, 1966]:

$$\sigma = \frac{E_s \cdot d_s^2 \cdot \Delta\delta}{3r^2(1 - v_s)d_f} \quad (2)$$

where $\sigma$ is the stress in the thin film, $\Delta\delta$ is the difference of the deflection $\delta$ at a point of radius r from the center of the substrate prior to and after film deposition, r is the radius of the point on the substrate, $d_s$ is the thickness of the substrate and $d_f$ is the film thickness, $E_s$ and $\nu$ are Young's modulus and Poisson's ratio of the substrate, respectively.

The deflection δ can be calculated according to the following formula:

$$\delta = \frac{0.6328}{4\pi}(\Phi_r - \Phi_c)$$

wherein $\Phi_r$ is a phase of the point on said substrate at the radius r from said central point thereof, and $\Phi_c$ is a phase of said central point of said substrate.

The calculation of the stress of the thin film including the phase functions of the substrate prior to and after the film deposition is performed in the PC in associated with programs developed by the inventors.

The internal stresses, σ, includes both the intrinsic stress ($\sigma_i$) produced during film deposition and the thermal stress ($\sigma_T$) mainly due to thermal expansion mismatch between the film and the substrate. The thermal stress can be written as:

$$\sigma_T = (\alpha_s - \alpha_f)\frac{E_f}{(1-\nu_f)}(T_2 - T_1)$$

wherein $\alpha_s$ is the thermal expansion coefficient of the substrate, $\alpha_f$ and $E_f$ are the thermal expansion coefficient and Young's modulus of the thin film, respectively, $\nu_f$ is Poisson's ratio of the thin film, $T_1$ is a deposition temperature of the thin film. In the present invention, the measuring temperature, $T_2$, is adjusted and controlled by using a temperature controller 110 connected to the substrate (test plate) 60 in the Twyman-Green interferometer shown in FIG. 1. The internal stress, σ, in the thin film measured by the TNyman-Green interferometer can be written as follows:

$$\sigma = \sigma_i + (\alpha_s - \alpha_f)\frac{E_f}{(1-\nu_f)}(T_2 - T_1) \quad (1)$$

From equation (1), it can be readily shown that the slope of the measured stress-temperature curve is equal to $$\frac{d\sigma}{dT} = (\alpha_s - \alpha_f)\frac{E_f}{1-\nu_f} \quad (3)$$

assuming that the values of $\alpha_s$, $\alpha_f$, $E_f$ and $\nu_f$ are independent of the temperature. In the absence of any information about either $\alpha_f$ or $$\frac{E_f}{1-\nu_f},$$

both values can be obtained by simply determining $d\sigma/dT$ on each of two substrates, with known values of $\alpha_s$, and solving two equations of the form of equation (3), for $\alpha_f$ and $$\frac{E_f}{1-\nu_f}$$

simultaneously. After knowing $\alpha_f$ and $$\frac{E_f}{1-\nu_f},$$

the intrinsic stress, $\sigma_i$, of the thin film can be calculated from equation (1).

EXAMPLE

Substrates

In the present example, BK-7 and Pyrex glass (Corning Inc.) substrates, with known thermal expansion coefficients and Young's moduli were used. Two pieces of glass were polished on one side to a flatness of one wavelength and ground on the other side. The stresses were measured for films deposited on the polished face of the two glass substrates (25.4 mm in diameter, 1.5 mm in thickness). The glass substrates used in the experiments were first carefully cleaned with detergent. A final cleaning was made with acetone using an ultrasonic cleaner.

$Ta_2O_5$ Preparation $Ta_2O_5$ thin films were deposited on unheated BK-7 and Pyrex substrates in a cryo-pumped vacuum chamber by ion beam sputter deposition (IBSP). In the IBSD process, oxygen was fed near the substrate, regulated by a needle valve. Before each deposition the vacuum chamber was pumped down to a base pressure of less than $6.0 \times 10^{-7}$ Torr. The oxygen partial pressure was $3.0 \times 10^{-5}$ Torr. The background pressure during the deposition was maintained at approximately $1.0 \times 10^{-4}$ Torr. The ion beam voltage was 950 V and the ion current was 30 mA. The system was equipped with a quartz crystal and an optical monitor for deposition rate and film thickness control. During the thin film deposition, the temperature of the two substrates was cooled to the ambient temperature. The optical constants of thin films were determined by the envelope method [SWANEPOEL, R.,1983, J. Phys. E, 16, 1214–1222] of optical transmission measurement. The thickness of the $Ta_2O_5$ thin films used for stresses measurement was 0.299 μm. The refractive index and the extinction coefficient were 2.16 and $1.15 \times 10^{-3}$, respectively.

Stress Measurement

The method for the measurement of stresses in films described above and the apparatus depicted in FIG. 1 were used. The tenperatures in all the experiments were determined to a tenth of a degree Celsius. The glass substrates were placed on a hot stage linked with an electric temperature controller 110. Interference fringes of reflected light between the reference plate 50 and the substrate 60 were detected with the CCD camera 80. The phase shifting fringe patterns were obtained by moving the reference plate 50 so five equally spaced positions of 79 nm, with a computer-controlled piexoelectric transducer (PZT) translation device 100. A programmable power supply controlled by the personal computer PC provided the PZT voltage.

The material constants of the substrates used in calculations of the elastic modulus and the thermal expansion coefficient of the films are given in Table 1. We assume that these material constants are independent in the temperature range from 25 to 70° C.

TABLE 1

| Substrates | Young's modulus (GPa) | Poisson's ratio | CTE (° C.$^{-1}$) |
|---|---|---|---|
| BK-7 | 81.0 | 0.208 | $7.40 \times 10^{-6}$ |
| Pyrex | 62.7 | 0.200 | $3.25 \times 10^{-6}$ |

Results and Discussions

Figure 2:
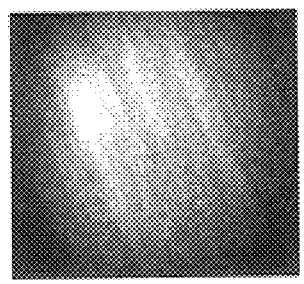
FIGS. 2(a1) to 2(c2) are phase shifting interferograms of 0° and 180° phase shifts for $Ta_2O_5$ deposited on a BK-7 glass substrate at elevated temperatures, wherein (a1) and (a2) are phase shifting interferograms of 0° and 180° phase shifts at 25° C.; (b1) and (b2) are phase shifting interferograms of 0° and 180° phase shifts at 50° C. and (c1) and (c2) are phase shifting interferograms of 0° and 180° phase shifts at 70° C.
Figure 2:
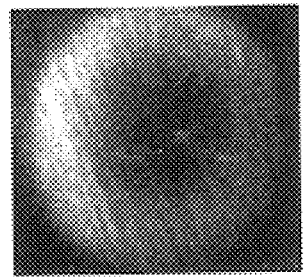
Figure 2:
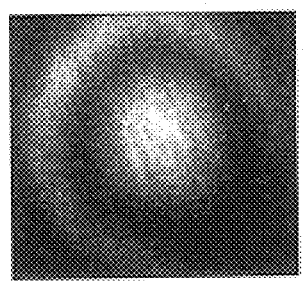
Figure 2:
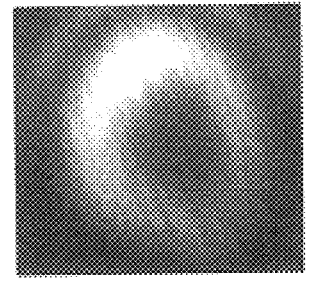
Figure 2:
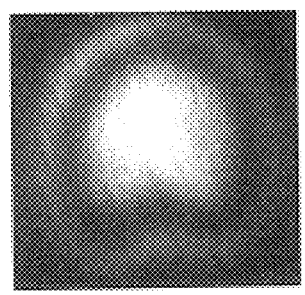
Figure 2:
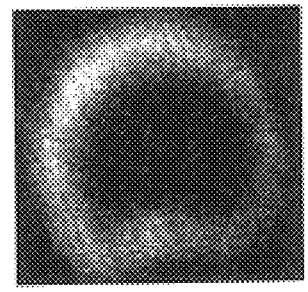
Figure 3:
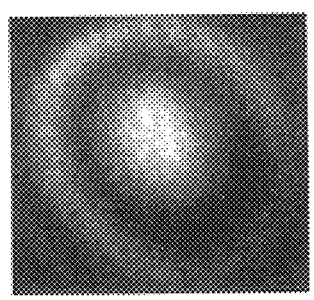
FIGS. 3(a1) to 3(c2) are phase shifting interferograms of 0° and 180° phase shifts for $Ta_2O_5$ deposited on a Pyrex glass substrate at elevated temperatures, wherein (a1) and (a2) are phase shifting interferograms of 0° and 180° phase shifts at 25° C.; (b1) and (b2) are phase shifting interferograms of 0° and 180° phase shifts at 50° C. and (c1) and (c2) are phase shifting interferograms of 0° and 180° phase shifts at 70° C.
Figure 3:
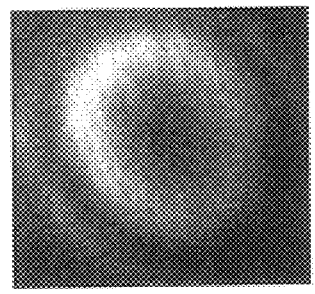
Figure 3:
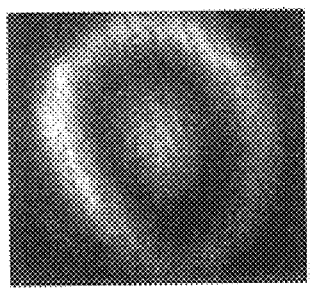
Figure 3:
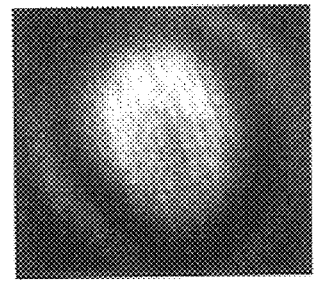
Figure 3:
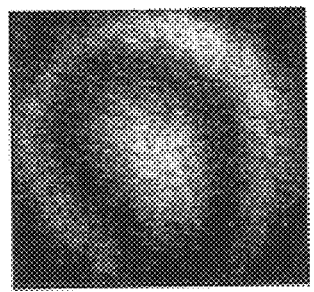
Figure 3:
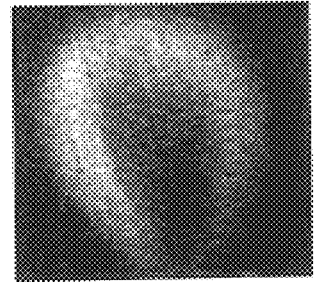
Figure 4:
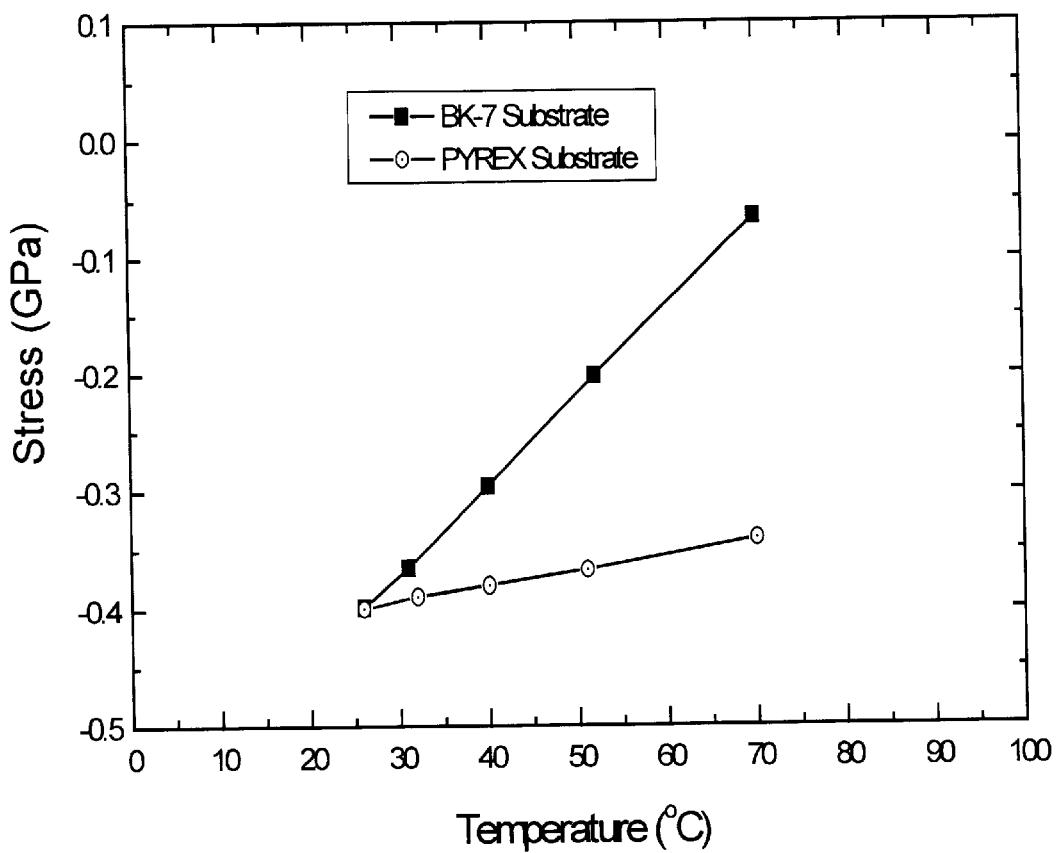
FIG. 4 is a plot showing the vz ition of stress with respect to the measurement temperature in $Ta_2O_5$ films deposited on two different substrates, wherein the black square dots represent results from the BK-7 substrate and the round circles represent the Pyrex substrate.

The temperature of the sample was controlled in the range from room temperature to 70° C. The interference fringes were recorded by a frame grabber 90. The change in the deformation of the substrates after deposition indicated strain in the films, which in turn is a measurement of stress in the film. By using phase shift interfereometry (PSI), interference fringe patterns having 0° and 180° phase shifts after the $Ta_2O_5$ film was deposited on the BK-7 glass substrate, varied from a uniform circular to distorted concentric rings, with temperature increases from room temperature to 70° C., as shown in FIGS. 2(a1) to 2(c2). similarly, the interference fringe patteyns of the 0° and 180° phase shifts after the $Ta_2O_5$ film was deposited on the Pyrex glass substrate, with temperature increases up to 70° C., are shown in FIGS. 3(a1) to 3(c2). The phase in the interferograms avas calculated using Hariharam's algorithm. This required five interferograms of digitized intisity with a constant phase difference. After the phase map data wew fitted by means of the Zernike polynomials, a contour map of the bare substrate and the coated substrate may be obtained. They show that the shape of th bare BK-7 substrate is upwardly concave while this bare Pyrex substrate is convex. After film deposition, the shape of the BK-7 coated substrate is less concave and presents $Ta_2O_5$ film stress under compression, but the shape of the Pyrex coated substrate is more convex, also showing $Ta_2O_5$ film under compression. We checked the fringe changes in FIGS. 2(a1) to 2(c1) and FIGS. 2(a2) to 2(c2) which got the same results. Subtracting the deformation of the coated substrate from the bare substrate, the deflection of the thin films may be obtained. The average deflection is calculated by the deformations at a distance of r=10 mm from the center of a circular substrate. The film stress can be derived from the average deflection by using equation (2). The stress of $Ta_2O_5$ film, deposited on the BK-7 glass substrate, varied from −0.398 to −0.064 GPa as the temperature increased from 25 to 70° C. In this case, the compressive stress in the films was observed to decrease after heating. The stress of $Ta_2O_5$ film deposited on a Pyrex glass substrate varied from −0.399 to −0.340 GPa, for the same temperature range. In both cases, upon heating, the stresses tend to get more tensile, indicating that the films have a smaller coefficient of thermal expansion $\alpha_f$ than the glass substrates. The decrease in the compressive stress may be attributed to the effect of stress relaxation. Finally, the internal stresses of $Ta_2O_5$ films deposited on BK-7 and Pyrex glass substrates are plotted against the stress measuring temperature as shown in FIG. 4. These samples were deposited at the same time to avoid any differences in the depositioci conditions.

In equation (1) the values of $\alpha_f$ and $$\frac{E_f}{1-v_f},$$

are unknown. As the intrinsic stress does not depend on the measurement temperature, the intrinsic stress, $\sigma_i$, can be calculated from the temperature dependence of the internal stress σ, assuming that $E_f$, $v_f$, $\alpha_f$, $E_s$, $v_s$ and $\alpha_s$ are temperature independent. The thermal expansion coefficient and the elastic modulus $$\frac{E_f}{1-v_f}$$

of thin film can be derived from the slope of the stress-temperature plot using at least two sorts of substrates, with known thermal expansion coefficients and Young's moduli. The stress-temperature curves for the films on the two different substrates have different slopes, as shown in FIG. 4. This is mainly because of a thermal mismatch between films on the two different substrates. The thermal mismatch is caused by the different thermal expansion coefficients of the films and the substrates. The slope of the line for the difference data is determined by least squares fitting. From the difference in the slopes of the two lines in FIG. 4, the average intrinsic stress, $\alpha_f$ and $$\frac{E_f}{1-v_f},$$

are calculated being −0.40 GPa, $2.42 \times 10^{-6}$ $C.^{-1}$ and 1549.4 GPa, respectively.

What is claimed is:

1. A method for measuring a thermal expansion coefficient of a thin film deposited on a substrate by phase shifting interferometry comprising the following steps:
   a) measuring a phase function of a target surface of a first substrate at a first measuring temperature;
   b) depositing a thin film on said target surface of said first substrate;
   c) measuring a phase function of said thin film by using the same conditions as those in step a);
   d) calculating one or more relative heights of one or more points with respect to a central point of said substrate prior to and after the deposition in step b) by using the phase functions obtained in steps a) and c, respectively, and calculating a difference of the relative heights at a savie point prior to and after the deposition in step b) for each of said one or more points;
   e) calculating a stress of said thin film for each of said one or more points by using said difference from step d) and calculating an average stress of said thin film therefrom;
   f) obtaining another on or more average stresses of said thin film of another one or more measuring temperatures by repeating steps a), c), d) and e) except that said first measuring temperature is replaced by said another one or more temperatures, and obtaining a first set of data of said average stresses versus said measuring temperatures with respect to said first substrate;
   g) measuring a phase function of a target surface of a second substrate at a second measuring temperature, wherein the second substrate has a thermal expansion coefficient different from that of said first substrate;
   h) depositing a thin film on said target surface of said second substrate with the conditions same as those in step b);
   i) measuring a phase function of said thin film in step h) by using the same conditions as those in step g);
   j) calculating one or more relative heights of one or more points with respect to a central point of said substrate prior to and after the deposition in step h) by using the phase functions obtained in steps g) and i), respectively, and calculating a difference of the relative heights at a same point prior to and after the deposition in step h) for each of said one or more points;
   k) calculating a stress of said thin film of step h) for each of said one or more points by using said difference from step j) and calculating an average stress of said thin film of step h) therefrom;
   l) obtaining another one or more average stresses of said thin film of step h) of another one or more measuring temperatures by repeating steps g), i), j) and k) except that said second measuring temperature is replaced by said another one or more temperatures, and obtaining a second set of data of said average stresses versus said measuring temperatures with respect to said second substrate; and m) calculating a thermal expansion coefficient, $\alpha_f$, of said thin film by using said first set data and said second set data.

2. The method according to claim 1, wherein said thermal expansion coefficient, $\alpha_f$, is calculated according to the following formula (1):

$$\sigma = \sigma_i + (\alpha_s - \alpha_f)\frac{E_f}{(1-v_f)}(T_2 - T_1) \quad (1)$$

wherein $T_2$ is any one said measuring temperatures, $\sigma$ is said average stress of said thin film at $T_2$, $\sigma_i$ is an intrinsic stress of said thin film, $\alpha_s$ is a thermal expansion coefficient of said first substrate or said second substrate, $E_f$ is a Young's modulus of said thin film, $v_f$ is a Poisson's ratio of said thin film, $T_1$ is a temperature at which said thin film is deposited in step b) and step h).

3. The method according to claim 2, wherein an elastic modulus defined as follows is obtained in step m) together with said thermal expansion coefficient, $\alpha_f$:

$$\frac{E_f}{(1-v_f)}$$

wherein $E_f$ and $v_f$ are defined as in claim 2.

4. The method according to claim 2, wherein said intrinsic stress, $\sigma_i$, of said thin film is obtained in step m) together with said thermal expansion coefficient, $\alpha_f$.

5. The method according to claim 4, wherein one of said measuring temperatures ($T_2$) is chosen to be equal to said temperature ($T_1$) at which said thin film is deposited in step b) and step h), so that said intrinsic stress, $\sigma_i$, is equal to said average stress of said thin film at $T_2$, $\sigma$, according to the formula (1).

6. The method according to claim 1, wherein said measurement of phase function in step a), c), g) and i) comprises the following steps:

I) generating two reflection light beams from a reference plate and a target surface of a substrate by perpendicularly irradiating two light beams splitted from one light source on said reference plate and said target surface;

II) recombining said two reflection light beams into one single beam and directing said one single beam on a screen to form an interference pattern;

III) digitizing said interference pattern to obtain digitized light intensities thereof;

IV) moving said reference plate or said substrate to several positions in a direction parallel to said light beam irradiating thereon, and said several positions being equally spaced from an original position of said reference plate or said substrate;

V) repeating steps I) to III) to obtain digitized light intensities of interference pattern for each one of said several positions; and VI) calculating a phase function of said target surface of said substrate by using said light intensities of said interference patterns obtained from step III) and step V).

7. The method according to claim 6, wherein said reference plate is moved to said several positions in step IV) by using a piezoelectric transducer (PZT) connected to a surface of said reference plate opposite to said light beam irradiating thereon, and by using a DC power supply controlled by a computer to supply a pre-determined voltage to said PZT.

8. The method according to claim 7, wherein said digitizing said interference pattern to obtain light intensity thereof in step III) comprises forming a image of said interference.pattern by using a CCD camera and digitizing a light intensity of each pixel of said image.

9. The method according to claim 8, wherein said digitized light intensities are provided to said computer, said phase functions in steps a), c), g) and i), said relative heights and said differences in steps d) and j), and said stress and said average stress in steps e) and k) are calculated by using said computer in associated with programs stored therein.

10. The method according to claim 9, wherein said reference plate is moved to four positions in step IV) which are equally spaced of $\lambda/8$ from an original position of said reference plate, wherein $\lambda$ is a wavelength of said irradiating light beam on said reference plate, so that five set of light intensities of said interference patterns in steps III) and V) representing 0°, 90°, 180°, 270°, and 360° phase shifts are obtained, and said phase function is calculated by the following formula:

$$\Phi = \tan^{-1}\left[\frac{2(I_2 - I_4)}{2I_3 - I_5 - I_1}\right]$$

wherein $I_1$, $I_2$, $I_3$, $I_4$ and $I_5$ represent said digitized light intensities at a particular pixel of the five interference patterns, and $\Phi$ is a phase of said particular pixel.

11. The method according to claim 10, wherein said relative heights in steps d) and j) are calculated according to the following formula:

$$\text{relative height} = \frac{0.6328}{4\pi}(\Phi_r - \Phi_c)$$

wherein $\Phi_r$ is a phase of a point on said substrate at a radius r from said central point thereof, and $\Phi_c$ is a phase of said central point of said substrate.

12. The method according to claim 11, wherein said stress of said thin film in steps e) and k) is calculated by the following formula:

$$\sigma = \frac{E_s \cdot d_s^2 \cdot \Delta\delta}{3r^2(1-v_s)d_f}$$

wherein $\sigma$ is a stress of said thin film on said substrate at a point of a radius r from said central point of said substrate;

$\Delta\delta$ is a difference of the relative heights at said point r prior to and after the deposition in steps b) and h);

r is the radius of the point from said central point of said substrate;

$d_s$ is the thickness of said substrate;

$d_f$ is the thickness of said thin film;

$E_s$ is a Young's modulus of said substrate; and $v_s$ is a Poisson's ratio of said substrate.

13. The method according to claim 6, wherein said light source in step I) is a laser light.

14. The method according to claim 6, wherein said light source is a slit light source generated by passing a light through a slit.

15. The method according to claim 1 further comprising repeating steps g) to m) for one or more substrates having different thermal expansion coefficients different from those of the first and second substrates, so that additional sets of data of said average stresses versus said measuring temperatures with respect to said one or more substrates are obtained, and so that said thermal expansion coefficient, $\alpha_f$, of said thin film can be calculated by using said additional sets of data together with said first set data and said second set data.

* * * * *